United States Patent [19]

Rocklage et al.

[11] Patent Number: 5,130,437
[45] Date of Patent: Jul. 14, 1992

[54] N,N'-BIS-(PYRIDOXAL)ETHYLENEDIA-MINE-N,N'-DIACETIC ACID DERIVATIVES

[75] Inventors: Scott M. Rocklage, Saratoga; Steven C. Quay, Los Altos Hills, both of Calif.

[73] Assignee: Salutar, Inc., Sunnyvale, Calif.

[21] Appl. No.: 578,265

[22] Filed: Sep. 6, 1990

Related U.S. Application Data

[62] Division of Ser. No. 380,185, Jul. 14, 1989, Pat. No. 4,994,259, which is a division of Ser. No. 47,584, May 8, 1987, Pat. No. 4,935,518.

[51] Int. Cl.$^5$ ............... C07D 213/66; C07D 213/67
[52] U.S. Cl. ........................ 546/261; 546/5; 546/6; 546/24
[58] Field of Search ............ 546/261, 6, 5; 424/9

[56] References Cited

U.S. PATENT DOCUMENTS

| | | | |
|---|---|---|---|
| 4,877,600 | 10/1989 | Bonnemain et al. | 424/4 |
| 4,880,007 | 11/1989 | Sadler et al. | 128/653 |
| 4,935,518 | 6/1990 | Rocklage et al. | 546/6 |
| 4,994,259 | 2/1991 | Rocklage et al. | 424/9 |

OTHER PUBLICATIONS

Chem. Abstract, The American Chemical Society, vol. 100, No. 20, pp. 389 May 14, 1984.
Chem. Abstract, The American Chemical Society, vol. 103, No. 6, p. 428 Aug. 12, 1985.
DeCola, et al; Inorg. Chem., 25, 1729-32 (1986).
Smith, et al.; J. Am. Chem. Soc., 111, No. 19, 7437-43 (1989).

Primary Examiner—Alan L. Rotman
Attorney, Agent, or Firm—Cushman, Darby & Cushman

[57] ABSTRACT

Manganese(II) chelates of N,N'-bis-(pyridoxal)alkylenediamine-N,N'-diacetic acids, N,N'-bis-(pyridoxal)-1,2-cycloalkylenediamine-N,N'-diacetic acids, N,N'-bis-(pyridoxal)-1,2-arylenediamine-N,N'-diacetic acids, N,N'-bis-(pyridoxal)alkylenediamine-N-acetic acids, N,N'-bis-(pyridoxal)-1,2-cycloalkylenediamine-N-acetic acids, N,N'-(pyridoxal)-1,2-arylenediamine-N-acetic acids, and their salts are highly stable, superior NMRI contrast agents. They maintain the manganese(II) ion in the +2 valence state. Preferred contrast agents are manganese(II) ion chelates of N,N'-bis-(pyridoxal)ethylenediamine-N,N'-diacetic acid, N,N'-bis-(pyridoxal)trans-1,2-cyclohexylenediamine-N,N'-diacetic acid, and the salts and esters thereof.

Novel chelate forming compounds are the N,N'-bis-(pyridoxal)-1,2-cycloalkylenediamine-N,N'-diacetic acids and N,N'-bis-(pyridoxal)-1,2-arylenediamine-N,N'-diacetic acids, N,N'-bis-(pyridoxal)alkylenediamine-N-acetic acids, N,N'-bis(pyridoxal)-1,2-cycloalkylenediamine-N-acetic acids, N,N'-bis-(pyridoxal)-1,2-arylenediamine-N-acetic acids, and their salts and esters.

9 Claims, 1 Drawing Sheet

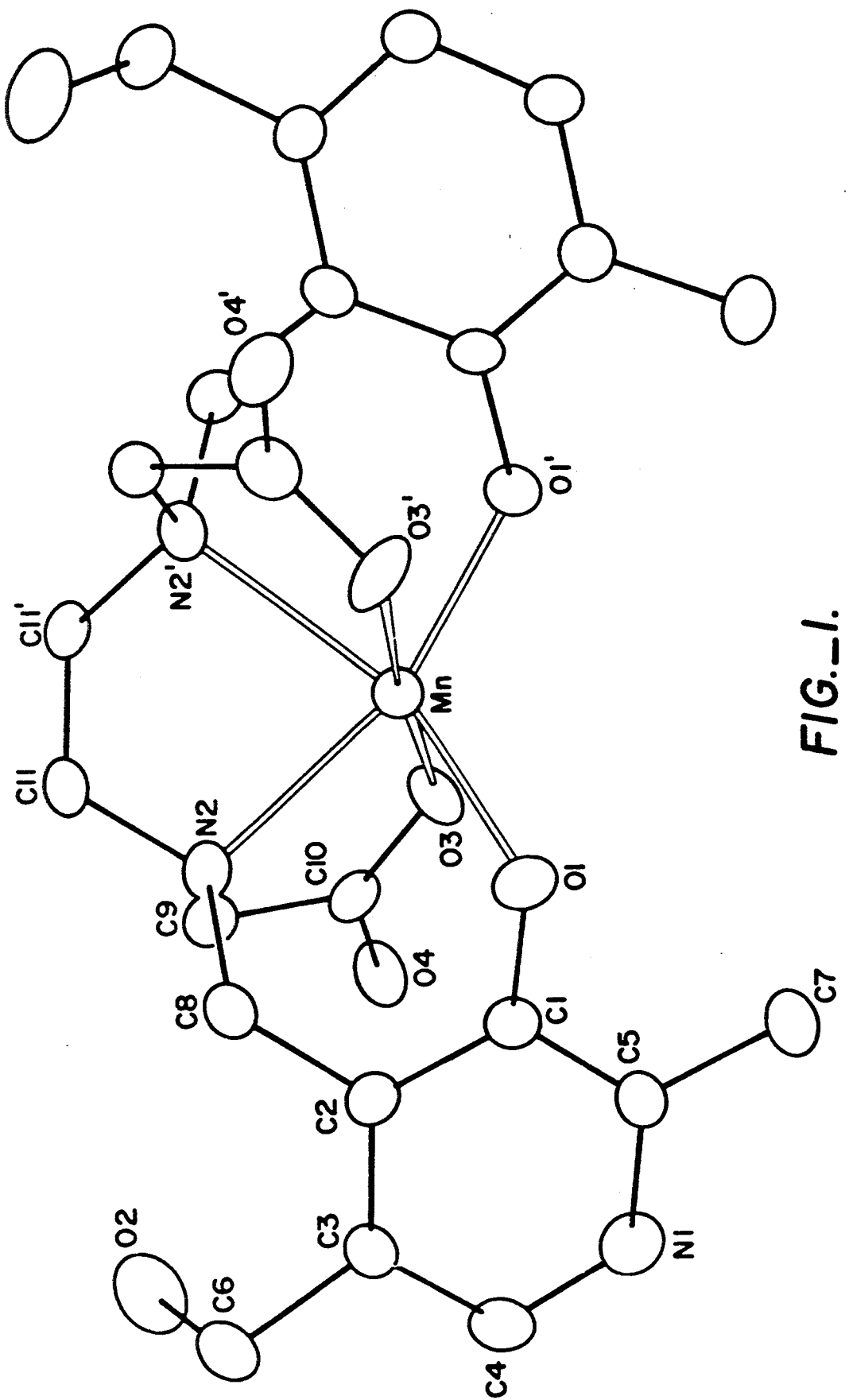
FIG._1.

N,N'-BIS-(PYRIDOXAL)ETHYLENEDIAMINE-N,N'-DIACETIC ACID DERIVATIVES

This application is a division of copending U.S. Pat. application Ser. No. 07/380185, filed Jul. 14, 1989, now U.S. Pat. No. 4,994,259, which in turn is a division of allowed U.S. Pat. application Ser. No. 07/047,584, filed May 8, 1987, now U.S. Pat. No. 4,935,518.

FIELD OF THE INVENTION

This invention relates to novel manganese(II) chelates and their use as contrast agents in nuclear magnetic resonance imagery (NMRI). In particular, this invention is directed to manganese(II) chelates of N,N'-dipyridoxyldiamine-N,N'-diacetic acid, and salts and esters thereof, and to the use of these compounds as contrast agents in NMRI methods.

BACKGROUND OF THE INVENTION

Traditionally, chelates have been used to administer poorly soluble salts in medicine and as antidotes for detoxification in cases of heavy metal or heavy metal isotope poisoning. Chelates have also been used to deliver radioisotopics to areas of the body for imaging and radiation therapy. Most recently, chelates with paramagnetic contrast agents have been reported for use as contrast agents in NMRI.

Paramagnetic metal ions are frequently toxic in the concentrations required for use in NMRI, and introducing them into the body in the form of chelates renders them more physiologically acceptable. This requires that a chelate be able to hold the metal ion tightly in the chelate structure, that is, the formation constant for the chelate must be very large at physiological pH. The paramagnetic metal chelate must also be sufficiently soluble to permit administration of quantities required for imaging in reasonably volumes of liquid. Usual routes of administration are oral, intravenous and by enema.

Since some paramagnetic metal ions may be released into the body, even from suitably stable chelates, paramagnetic metal ions which are naturally present in the body should be preferred. Manganese is naturally present in the body in trace quantities, and manganese(II) ions would be desirable paramagnetic materials if they could be formed into stable, soluble chelates. However, because manganese(II) is unstable in the presence of either reducing or oxidizing agents, the use of any chelating agent with an oxidizing or reducing group with manganese(II) was believed to be futile because redox reactions of the Mn(II)-chelate.

This invention provides a novel, highly stable manganese(II) chelate which meets the above objectives.

DESCRIPTION OF THE PRIOR ART

A summary of the history and state of the art of contrast agents for NMRI are presented by Valk, J. et al., *BASIC PRINCIPLES OF NUCLEAR MAGNETIC RESONANCE IMAGING*, New York: Elsevier, pp 109–114 (1985). The Valk et al publication also describes the imaging equipment and methods for NMRI, and the entire contents of the Valk et al publication are hereby incorporated by reference in its entirety. Chelates of iron, manganese, and gadolinium with ethylenediaminetetraacetic acid (EDTA) and diethylaminetriaminepentaacetic acid (DTPA) are described. Gadolinium, however, is not naturally present in the body and long term toxicity studies have not been completed. Paramagnetic materials listed in this publication include molecules with unpaired electrons: nitric oxide (NO); nitrogen dioxide ($NO_2$); and molecular oxygen ($O_2$). Also included are ions with unpaired electrons, that is ions from the "transition series". Listed ions include $Mn^{2+}$, $Mn^{3+}$, $Fe^{2+}$, $Fe^{3+}$, $Ni^{2+}$, $Cr^{2+}$, $Cu^{2+}$, the lanthanide series including gadolinium and europium, and nitroxide stable free radicals (NSFR) such as pyrrolidine NSFR and piperidine NSFR. Toxicity problems are indicated to present a major problem with many paramagnetic materials.

Use of alkylenediamine chelates with a variety of paramagnetic ions are described in U.S. Pat. No. 4,647,447. Ferrioxamine-paramagnetic contrast agents are described in U.S. Pat. No. 4,637,929. Manganese(II) is included in a list of suitable paramagnetic metal ions for use with polysaccharide derivatives of a variety of chelating compounds including EDTA, DTPA and aminoethyl diphosphonate in PCT application publication no. WO85/05554 (Application No. PCT/GB85/00234). Stable radioactive diagnostics agents containing $^{99m}Tc$ chelated with N-pyridoxal-alpha-aminoacids or a pyridoxal salt are disclosed in U.S. Pat. Nos. 4,313,928, 4,440,739, and 4,489,053.

Taliaferro, C. et al in "New multidentate ligands. 22. N,N'-dipyridoxyethylenediamine-N,N'-diacetic acid: a new chelating ligand for trivalent metal ions", *Inorg. Chem.* 23 1188–1192 (1984) describe development of N,N'-dipyridoxyethylenediamine-N,N'-diacetic acid (PLED) as a chelating compound for trivalent ions. Other chelating compounds described are the Fe(III) chelates of N,N'-ethylenebis-2-(o-hydroxyphenyl)glycine (EHPG) and N,N-'bis(1-hydroxybenzyl)ethylenediamine-N,N'-diacetic acid (HBED). Properties of chelates of PLED, HBED, EHPG and EDTA with ions of copper, nickel, cobalt, zinc, iron indium and gallium are compared. Investigation of the structure of PLED is reported by Taliaferro, C. et al., *Inorg.Chem.* 24:2408–2413 (1985). Green, M. et al, *Int.J.Nucl.Med.-Biol.* 12(5):381–386 (1985) report their evaluation of PLED as a chelating ligand for the preparation of gallium and indium radiopharmaceuticals, and summarize properties of PLED chelates with Ga(III), In(III), and Fe(III).

Because the compounds of this invention have an aromatic hydroxy group, their value as a chelating agents for manganese(II) ions would not be expected; such aromatic hydroxy groups would be expected to react with the manganese(II) ion as an oxidant in the usual way, oxidizing the manganese(II) ion to a higher valence. Frost, et al., *J.Am.Chem.Soc.* 80:530 (1958) report the formation of Mn(II) chelates of EHPG at low pH, but found that attempts to prepare stable manganese(II) complexes with EHPG at higher pH's (above pH 5) was futile as the manganese(II) ion was irreversibly oxidized. This oxidation occurred even under inert atmospheres, and the writers concluded that the oxidation occurred at the expense of the ligand or solvent. Anderegg, G. et al, *Helv.Chim.Acta.* 47:1067 (1964) found the high stability of the Fe(III) chelate of EHPG was due to the high affinity of the Fe(III) ion for the two phenolate groups present in the ionized ligand.

L'Eplathenier, F. et al., (*J.Am.Chem.Soc.* 89:837 (1967) describes studies of HBED involving acid titrations of HBED in the presence of a variety of metal ions, including manganese(II). No manganese chelate was isolated, and the manganese products were not characterized. Based on subsequent work by Patch et al, *Inorg. Chem.* 21(8):2972-2977 (1982), it is clear that the manganese(II) ion was oxidized by the phenolic ligand during the titrations of L'Eplathenier et al. Patch et al prepared a Mn(III) complex by reacting Mn(II) salts with EHPG, and concluded the reaction involved the oxidation of the ligand in an irreversible reaction. The ability of maintain Mn(III) in the +3 oxidation state was said to be a unique characteristic of the EHPG molecule. U.S. Pat. No. 3,632,637 describes phenolic chelating agents such as N,N-di(o-hydroxylbenzyl)-ethylenediamine-N,N'-diacetic acid and their use in chelating trivalent and tetravalent metals which are usually stable in the presence of aromatic hydroxy groups. No use of a compound with an aromatic hydroxy group as a chelating agent for manganese(II) ions is disclosed in these references, confirming the general knowledge about the oxidizing properties of the aromatic hydroxy group on manganese compounds, in particular manganese(II) ions.

SUMMARY OF THE INVENTION

The novel chelates of this invention are chelates of manganese(II) with a compound of Formula I.

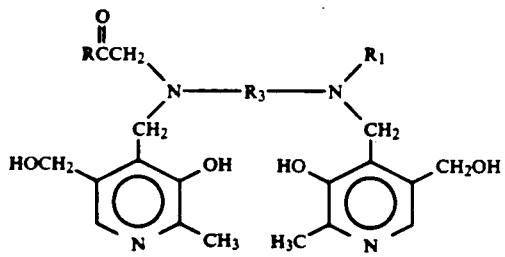

(I)

wherein
R is hydroxy, alkoxy having from 1 to 18 carbons, hydroxy-substituted alkoxy having from 1 to 18 carbons, amino or alkylamido having from 1 to 18 carbons;
$R_1$ is hydrogen or

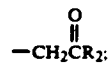

$R_2$ is hydroxy, alkoxy having from 1 to 18 carbons, amino or alkylamido having from 1 to 18 carbons; and
$R_3$ is alkylene having from 1 to 8 carbons, 1,2-cycloalkylene having from 5 to 8 carbons, or 1,2-arylene having from 6 to 10 carbons.

The pharmaceutically acceptable water-soluble compatible salts of these chelates are also included within the chelates of this invention.

BRIEF DESCRIPTION OF THE DRAWING

FIG. 1 is an isometric representation of a molecular model of the PLED-Mn$^{+2}$ chelate complex as determined in Example 7, showing the spatial relationships between the groups entering into chemical bonds with the manganese(II) ion.

DETAILED DESCRIPTION OF THE INVENTION

This invention is based on the discovery that manganese(II) forms a highly stable chelate with PLED, PLED analogs and PLED derivatives. Contrary to expectations based on the known interactions of aromatic hydroxy compounds and manganese(II) ions, the manganese(II) ion is not oxidized to a higher valence state in the PLED chelates.

Relatively few manganese(II) compounds are known, and only a fraction of these have been characterized, including single crystal X-ray diffraction work. Most of the structurally characterized Mn(II) complexes have various mono and bidentate ligand coordinating to the metal center. The Mn(II) complexes with PLED and the related 1,2-cycloalkylene and 1,2-arylene compounds are the first Mn(II) complexes with a high affinity hexadentate ligand. This configuration provides a more stable and effective form for introducing manganese(II) into the body as a NMRI contrast medium.

The novel manganese(II) chelates of this invention are formed from the compounds of Formula I.

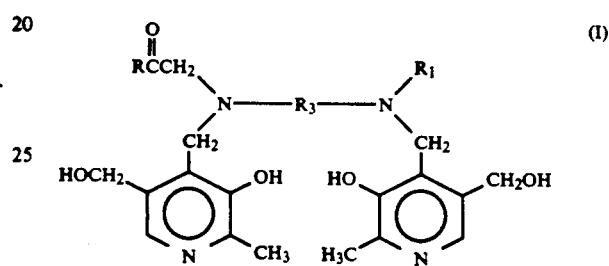

(I)

wherein
R is hydroxy, alkoxy having from 1 to 18 carbons, hydroxy-substituted alkoxy having from 1 to 18 carbons, amino or alkylamido having from 1 to 18 carbons;
$R_1$ is hydrogen or

$R_2$ is hydroxy, alkoxy having from 1 to 18 carbons, amino alkylamido having from 1 to 18 carbons; and
$R_3$ is alkylene having from 1 to 8 carbons, 1,2-cycloalkylene having from 5 to 8 carbons, or 1,2-arylene having from 6 to 10 carbons.

The pharmaceutically acceptable water-soluble compatible salts of the compounds of Formula I are also included within the chelate forming compounds of this invention.

In Formula I, R and $R_2$ are preferably each individually hydroxy, ethylene glycol, glycerol, alkoxy having from 1 to 8 carbons, amino or alkylamido having from 1 to 8 carbons. Optimally R and $R_2$ are hydroxy and the salts thereof.

The term "alkyl" as used herein includes both straight and branchchained, and saturated and unsaturated hydrocarbons. The term "1,2-cycloalkylene" includes both cis and trans cycloalkyl and alkyl substituted cycloalkyl groups bonded at the 1,2-positions to respective nitrogen atoms and alkyl substituted derivatives thereof having from 3 to 8 carbons. The term "1,2-arylene" includes phenyl and naphthyl groups bonded at the 1,2-positions to respective nitrogen atoms and alkyl substituted derivatives thereof having from 3 to 10 carbons.

For purposes of clarity, the chelates of this invention will be described hereinafter in terms of the manganese(II) ion chelate of PLED. However, this is for purposes of clarity of explanation and not by way of limitation, and chelates of all of the compounds of Formula I are included within the scope of this invention.

Since not all of the acidic protons of the chelates are substituted by the central paramagnetic ion, the solubility of the chelate can be increased if the remaining protons are converted to salts of the conjugate base with physiologically biocompatible cations of inorganic and/or organic bases or amino acids. For example, the lithium ion, the sodium ion and especially the calcium ion are suitable inorganic cations. Suitable cations of organic bases include, for example, ethanolamine, diethanolamine, morpholine, glucamine, N,N-dimethylglucamine, N-methylgulcamine. Lysine, arginine or orithine are suitable cations of amino acids, as generally are those of other bases of naturally occurring acids.

The chelates of this invention can be represented by Formulas II and III.

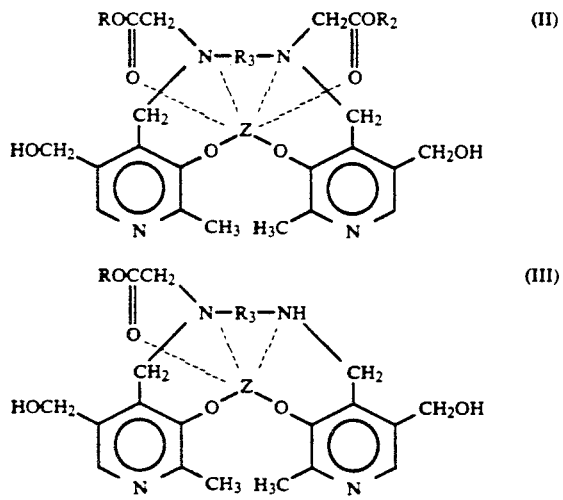

In Formulas II and III, Z represents a metal ion and $R_1$, $R_2$ and $R_3$ are the same as described with respect to the compounds of Formula I. The dotted lines in the figures represent the dative bonding between the oxygen and nitrogen atoms and the metal ion. As can be seen in FIG. I, one of the acetyl groups (hydroxycarbonylmethyl groups or salts or esters thereof) of Formula II is below the plane of the aromatic pyridine rings and the other acetyl group is above the plane of the aromatic pyridine rings, so that metal ion is more tightly held within the interior of the chelate salt complex with the dicarboxy embodiments of this invention.

The chelates according to this invention are formed from the chelate forming compounds of Formula I by conventional procedures known in the art. In general, these processes involve dissolving or suspending the manganese(II) salt (for example, chloride or carbonate) in water or a lower alcohol such as methanol, ethanol or isopropanol. To this solution or suspension is added an equimolar amount of the chelating acid in water or a lower alcohol, and the mixture is stirred, if necessary, with heating moderately or to the boiling point, until the reaction is completed. If the chelate salt formed is insoluble in the solvent used, the reaction product is isolated by filtering. If it is soluble, the reaction product is isolated by evaporating the solvent to dryness, for example, by spray drying or lyophilizing.

If free acid groups are still present in the resulting chelate, it is advantageous to convert the acidic chelate salt into a neutral chelate salt by reaction with inorganic and/or organic bases or amino acids, which form physiologically biocompatible cations, and to isolate them. This is often unavoidable since the dissociation of the chelate salt is moved toward neutrality to such an extent by a shift in the pH value during the preparation that only in this way is the isolation of homogeneous products or at least their purification made possible. Production is advantageously performed with organic bases or basic amino acids. It can also be advantageous, however, to perform the neutralization by means of inorganic bases (hydroxides, carbonates or biocarbonates) of sodium, potassium or lithium.

To produce the neutral salts, enough of the desired base can be added to the acid chelate salts in an aqueous solution or suspension that the point of neutrality is reached. The resulting solution can then be concentrated to dryness in vacuo. It is often advantageous to precipitate the neutral salts by adding solvents miscible with water, for example, lower alcohols (methyl, ethyl, isopropyl alcohols, etc.), lower ketones (acetone, etc.), polar ethers (tetrahydrofuran, 1,2-dimethoxyethane, etc.) and thus obtain crystals that isolate easily and purify well. It has been found particularly advantageous to add the desired bases to the reaction mixture even during chelating and thus eliminate a process stage. Other conventional purification procedures such as column chromatography can be used.

Since the chelate salts of Formula II contain two carboxylic acid groups, it is possible to produce neutral mixed salts which contain both inorganic and organic physiologically biocompatible cations as counterions. This can be done, for example, by reacting the complexing acids in an aqueous suspension or solution with the oxide or salt of the element supplying the central ion or less than the full amount of an organic base necessary for neutralization, e.g., half, isolating the chelate salt that is formed, purifying it, if desired, and then adding it to the amount of inorganic base necessary for complete neutralization. The sequence of adding the bases can be reversed.

The diagnostic media for administration is formed using physiologically acceptable media in a manner fully within the skill of the art. For example, the chelate salts, optionally with the addition of pharmaceutically acceptable excipients, are suspended or dissolved in an aqueous medium, and then the solution or suspension is sterilized. Suitable additives include, for example, physiologically biocompatible buffers (as, for example, tromethamine hydrochloride), slight additions of other chelating agents (as for example, diethylenetriaminpentacetic acid) or, if necessary, calcium salts (for example, calcium chloride, calcium lactate, calcium gluconate or calcium ascorbate).

Alternatively, the diagnostic media according to this invention can be produced without isolating the chelate salts. In this case, special care must be taken to perform the chelating so that the salts and salt solutions according to the invention are essentially free of unchelated, potentially toxic metal ions. This can be assured, for example, using color indicators such as xylenol orange by control titrations during the production process. A purification of the isolated salt chelate can also be employed as a final safety measure.

If suspensions of the chelate salts in water or physiological salt solutions are desired for oral administration, a small amount of soluble chelate salt is mixed with one or more of the inactive ingredients traditionally present in oral solutions and/or surfactants and/or aromatics for flavoring.

The most preferred mode for administering paramagnetic metal chelates as contrast agents for NMRI analysis is by intravenous administration. Intravenous solutions must be sterile, free from physiologically unacceptable agents, and should be isotonic or iso-osmotic to minimize irritation or other adverse effects upon administration. Suitable vehicles are aqueous vehicles customarily used for administering parenteral solutions such as Sodium Chloride Injection, Ringer's Injection, Dextrose Injection, Dextrose and Sodium Chloride Injection, Lactated Ringer's Injection, and other solutions such as are described in REMINGTON's PHARMACEUTICAL SCIENCES. 15th Ed., Easton: Mack Publishing Co. pp 1405–1412 and 1461–1487 (1975) and THE NATIONAL FORMULARY XIV. 14th Ed. Washington: American Pharmaceutical Association (1975), the contents of which are hereby incorporated by reference. The solutions can contain preservatives, antimicrobial agents, buffers and antioxidants conventionally used in parenteral solutions, selecting excipients and other additives which are compatible with the chelates and which will not interfere with the manufacture, storage or use of the products.

The diagnostic media according to this invention can contain from 0.0001 to 5.0 moles per liter and preferably from 0.1 to 0.5 moles per liter of the chelate salt.

The chelates of this invention are administered to patients for imaging in amounts which are sufficient to yield the desired contrast. Generally, dosages of from 0.001 to 5.0 mmoles of contrast agent per kilogram of patient body weight are effective to achieve reduction of relaxivity rates. The preferred dosages for most NMRI applications are from 0.05 to 0.5 mmoles of contrast agent per kilogram of patient body weight.

Methods for applying the contrast agents to improve NMRI images, equipment and operating procedures are described by Valk, J. et al, supra. The contrast agents can be used orally and intravenously.

In a novel NMRI application, the contrast agents can be introduced into the cervix, uterus and fallopian tubes. NMR imaging can then be performed to detect causes of infertility such as obstructions or imperfections in the internal surface of the fallopian tubes which might interfere with the movement of the fertilized ovum.

CHELATE FORMING COMPOUNDS

The compounds of Formula I can be formed by reacting the the corresponding pydridoxal (3-hydroxy-2-methyl-4-pyridinecarboxyaldehyde) represented by Formula IV with an diamine represented by Formula V according to the procedure for making PLED described by Taliaferro, C. et al, *Inorg.Chem.* 23:1188–1192 (1984).

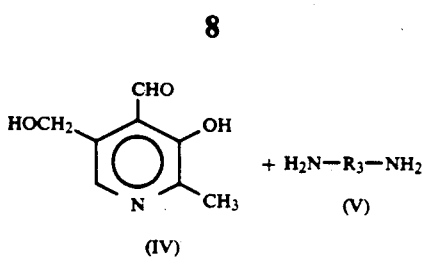

In the compounds of Formula V, $R_3$ represents an alkylene, 1,2-cycloalkylene group having from 3 to 8 carbons, and 1,2-arylene group having from 6 to 10 carbons. Pyridoxal, the compound of Formula IV, and the alkylenediamine, cycloalkylene and arylene reactants of Formula V are well known compounds readily available from commercial sources, and they can be readily synthesized by well known procedures fully within the skill of the art.

The reaction of the amino groups of the diamines of Formula V with the aldehyde group of pyridoxal can be carried out in an alcohol such as methanol at a temperature within the range of from 0° to 60° C. The product formed is represented by Formula IV.

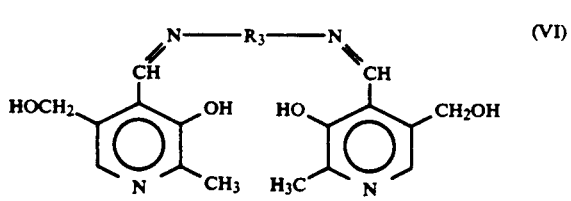

In the diimines of Formula VI, $R_3$ is the same as described with respect to the compounds of Formula I. The N,N'-dipyridoxylidenealkylenediimines, 4-(N-(2-methyl-3-hydroxy-5-hydroxymethyl-4-pyridinylmethylide)alkyleneiminomethyl)-2-hydroxy-3-methyl-5-pyridylmethanols; N,N'-dipyridoxylidene-1,2-cycloalkylenediimines, 4-(N-(2-methyl-3-hydroxy-5-hydroxymethyl-4-pyridinylmethylide)-1,2-cycloalkyleneiminomethyl)-2-hydroxy-3-methyl-5-pyridylmethanols; and N,N'-dipyridoxylidene-1,2-arylenediimines, 4-(N-(2-methyl-3-hydroxy-5-hydroxymethyl-4-pyridinylmethylide)-1,2-aryleneiminomethyl)-2-hydroxy-3-methyl-5-pyridylmethanols of Formula VI are insoluble in the alcohol and can be isolated by filtration.

The diimines of Formula VI are then hydrogenated by conventional procedures using a palladium or platinum catalyst to yield the diamines of Formula VII.

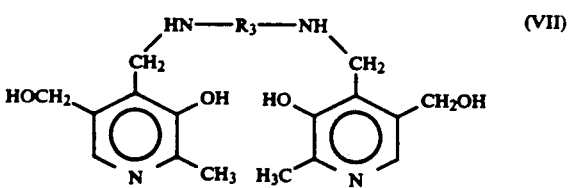

In the compounds of Formula VII, $R_3$ is the same as described with respect to the compounds of Formula I. The N,N'-dipyridoxylalkylenediamines, 4-(N-(2-methyl-3-hydroxy-5-hydroxymethyl-4-pyridinylmethyl)alkyleneaminoethyl)-2-hydroxy-3-methyl-5-pyridylmethanols; N,N'-dipyridoxy-1,2-cycloalkylenediamine, 4-(N-(2-methyl-3-hydroxy-5-hydroxymethyl-4-pyridinylmethyl)-1,2-cycloalkyleneaminomethyl)-2- hydroxy-3-methyl-5-pyridylmethanols; and N,N'-dipyridoxyl-1,2-arylenediamines, 4-(N-(2-methyl-3-hydroxy-5-hydroxymethyl-4-pyridinylmethyl)-1,2-aryleneaminomethyl)-2-hydroxy-3-methyl-5-pyridylmethanols of Formula VI can be left in solution or isolated.

The monoacetic and diacetic acid compounds of Formula I are prepared by reacting the diamines of Formula VII with haloacetic acid, preferably bromoacetic acid, the molar ratio of the bromoacetic acid to diamine determining whether one or both of the amines are conjugated with the acetic acid groups.

The N,N'-bis(3-hydroxy-2-methyl-5-hydroxymethyl-4-pyridylmethyl)alkylenediamine-N,N'-diacetic acids, N,N'-bis(3-hydroxy-2-methyl-5-hydroxymethyl-4-pyridylmethyl)-1,2-cycloaklylenediamine-N,N'-diacetic acids, N,N'-bis(3-hydroxy-2-methyl-5-hydroxymethyl-4-pyridylmethyl)-1,2-arylenediamine-N,N'-diacetic acids, N,N'-bis(3-hydroxy-2-methyl-5-hydroxymethyl-4-pyridylmethyl)alkylenediamine-N-acetic acids, N,N'-bis(3-hydroxy-2-methyl-5-hydroxymethyl-4-pyridylmethyl)-1,2-cycloalkylenedamine-N-acetic acids, and N,N'-bis(3-hydroxy-2-methyl-5-hydroxymethyl-4-pyridylmethyl)-1,2-arylenediamine-N-acetic acids of Formula I are then isolated and purified by conventional procedures such as anion exchange chromatography or recrystallization.

This invention is further illustrated by the following specific but non-limiting examples. Temperatures are given in degrees centigrade and concentrations as weight percents unless otherwise specified. Procedures which are constructively reduced to practice herein are described in the present tense, and procedures which have been carried out in the laboratory are set forth in the set tense.

EXAMPLE 1

N,N'-bis(pyridoxal)ethylenediimine

A 25 mg(0.123 mole) quantity of pyridoxal hydrochloride was slurried in 100 ml of methanol, and 4.88 gm (0.123 mole) of NaOH was added. When the solution was homogeneous, 3.75 gm of 1,2-diaminoethane (Aldrich Chem. Co.) was added rapidly with vigorous stirring. The imine product N,N'-bis(pyridoxal)ethylenediimine or 4-(N-92-methyl-3-hydroxy-5-hydroxymethyl-4-pyridinylmethlide)ehtyleneiminomethyl)-2-hydroxy- 3-methyl-5-pyridylmethanol was stirred for 1 hr, and the slurry which formed was filtered. The product was washed with methanol (2×50 ml) and diethyl ether (2×50 ml), and dried at 40° C. in vacuo to yield 23.6 gm (89% yield) of product. IR (KBr pellet): 1625 cm$^{-1}$ (C=N).

EXAMPLE 2

N,N'-bis(pyridoxal)alkyldiimines

Repeating the procedure of Example 1 but replacing the 1,2-diaminoethane with 1,3-diamino-n-propane, 1,2-diamino-n-propane, 1,2-diaminoisopropane, 1,2-diamino-n-butane, 1,4-diamino-n-butane, 1,3-diamino-n-butane, 1,2-diamino-3-methylpropane yields the corresponding N,N'-bis(pyridoxal)-1,3-(n-propylene)diimine, N,N'-bis(pyridoxal)-1,2-(n-propylene)diimine, N,N'-bis(pyridoxal)-1,2-isopropylenediimine, N,N'-bis(pyridoxal)-1,2-(n-butylene)diimine, N,N'-bis(pyridoxal)-1,4-(n-butylene)diimine, N,N'-bis(pyridoxal)-1,3-(n-butylene)diimine, and N,N'-bis(pyridoxal)-1,2-(3-methylene)propyldiimine.

EXAMPLE 3

N,N'-bis(pyridoxal)ethylenediamine

The diimine from Example 1 was charged to a one liter 3-neck flask fitted with mechanical stirrer, fritted tube bubbler, and a 3-way stopcock. Then 250 ml of deionized water was added, followed by 250 ml of methanol. The solution formed was stirred while sparging with nitrogen. Then 2 gm of 5% Pt on carbon (Aldrich Chem. Co.) was added, and the apparatus was purged with hydrogen. The reaction was allowed to proceed for 5 hr with continuous addition of hydrogen. Complete reduction to the amine was determined by HPLC analysis. The reaction mixture was sparged with nitrogen for 15 min and then filtered through Celite. The filtrate was concentrated in vacuo at 60° C. to about 100 ml. The solution, containing N,N'-bis(pyridoxal)ethylenediamine or 4-(N-(2-methyl-3-hydroxy-5-hydroxymethyl-4-pyridinyl-methyl)ethyleneaminomethyl)-2-hydroxy-3-methyl-5-pyridylmethanol can be used directly for the next step or the product can be isolated by crystallization from water. $^1$H NMR (D$_6$-DMSO, 400 MHz) delta 7.80 (s, pyr-H), 4.44 (s, pyr-CH$_2$OH), 4.01 (s, NCH$_2$CH$_2$N), 2.70 (s, N-CH$_2$-pyr), 2.30 (s, pyr-CH$_3$).

EXAMPLE 4

N,N'-bis(pyridoxal)alkyldiamines

Repeating the procedure of Example 3 but substituting the products of Example 2 for the diimine product of Example 1 yields N,N'-bis(pyridoxal)-1,3-(n-propylene)diamine, N,N'-bis(pyridoxal)-1,2-(n-propylene)diamine, N,N'-bis(pyridoxal)-1,2-isopropylenediamine, N,N'-bis(pyridoxal)-1,2-(n-butylene)diamine, N,N'-bis(pyridoxal)-1,4-(n-butylene)diamine, N,N'-bis(pyridoxal)-1,3-(n-butylene)diamine, and N,N'-bis(pyridoxal)-1,2-(3-methylene)propyldiamine

EXAMPLE 5

PLED Synthesis

The diamine for Example 3 was charged to a 500 ml 4-neck flask equipped with two addition funnels, pH electrode, thermometer and stir bar. A 12.0 gm (0.3 mole) quantity of NaOH was dissolved in 25 ml of deionized water, and 15.4 gm (0.11 mole) of bromoacetic acid (Sigma Chem. Co.) was dissolved in 25 ml of deionized water. Each solution was charged to an addition funnel. Enough NaOH solution was added to the diamine solution to bring the pH to 11. The temperature of the reaction was raised to 42° C., and bromoacetic acid and NaOH solution were added concurrently to maintain the pH at 11. The addition was stopped at 45 min, and the progress of the reaction was checked by HPLC. The addition of bromoacetic acid and NaOH was resumed, and the reaction checked at 60 and 75 min. All the bromoacetic acid had been added, and confirmation that the reaction was completed was determined by HPLC analysis. A 65 gm quantity of cation exchange resin (AMBERLITE IRC-50) was added, and the mixture was placed in a refrigerator for 14 hr. The resin was removed by filtration, and the filtrate treated with 15 gm of cation exchange resin (DOWEX 50W-X8). The resin was removed by filtration, and the solution was concentrated in vacuo at 60° C. to yield N,N'-bis-pyridoxalethylenediamine-N,N'-diacetic acid or N,N'-bis(3-hydroxy-2-methyl-5-hydroxymethyl-4-pyridylmethyl)ethylenediamine-N,N'-diacetic acid (PLED). The product was recrystallized from water/methanol. $^1$H NMR (D$_6$DMSO, 400 MHz) delta 7.773 (s, pyr-H), 4.57 (s, pyr-CH$_2$OH), 4.18 (s, NCH$_2$CH$_2$N), 3.27 (s, CH$_2$COOH), 2.98 (s, N-CH$_2$-pyr), 2.30 (s, pyr-CH$_3$).

EXAMPLE 6

Sodium Salt of Manganese(II)-PLED Chelate

A 4.16 gm (6.25 mmole) portion of PLED from Example 5 was dissolved in 50 ml of rigorously degassed water by the addition of 0.5 gm (12.5 mmoles) of NaOH. A 1.25 fm (6.25 mmole) quantity of manganese dichloride tetrahydrate was added. After stirring for 30 min, 0.25 gm (6.25 mmole) of solid NaOH was added to bring the pH up to 6.5. Then 0.15 gm (1.0 mmole) of calcium chloride was added, and sufficient degassed water was added to bring the volume of the solution to 250 ml. The solution was sterilized by being filtered through a 0.2 micron filter to yield the sodium salt of a manganese chelate complex of N,N'-bis-pyridoxalethylenediamine-N,N'-diacetic acid (PLED).

EXAMPLE 7

Structural characterization of Mn(II)-PLED

Crystals of Mn(II)-PLED were grown from an aqueous solution at pH 7. The orange colored crystals were found to lose their water of crystallization in dry air. A suitable crystal with the dimensions of 0.47×0.50×0.32 mm was mounted in a moist, thin-wall glass capillary and subjected to x-ray examination. The raw intensity data wa analyzed and the crystal structure schematically represented in Formula II and FIG. 1 was determined.

The crystal structure shows the Mn(II) chelate to consist of discrete molecules of manganese(II)-PLED. The Mn(II)-PLED and water molecules form an indefinite polymeric network via various hydrogen bonds. Mn(II) resides in the center of a distorted octahedron made up by two aromatic hydroxy oxygen atoms (01, 01'), two carboxylic a oxygen atoms (03, 03'), and two tertiary nitrogen atoms (N2, N2') as shown in FIG. 1. All four coordinating oxygen atoms are negatively charged. However, the two nitrogen atoms of the aromatic ring (N1, N1') are protonated, reducing the total charge of the ligand to −2, which indicates that the charge at the manganese atom is +2.

This assumption is corroborated by an inspection of the Mn-O and Mn-N bond distances. The ionic radius of hexaccordinated manganese decreases with increasing charge on the metal atom. Thus one would expect an Mn$^{+2}$—O distance of 2.180 angstrom and Mn$^{+3}$—O distances of not longer than 1.995. Both Mn—O separations in Mn(II)-PLED (Mn-01 2.0907 angstroms and Mn-03 2.2434 angstroms) are longer than expected for Mn$^{+3}$ and fall within the range predicted for Mn$^{+2}$.

Furthermore, the observed Mn-O separations in this crystal are in good agreement with previously reported Mn$^{+2}$—O distances: Mn—O (amide) 2.19 angstroms (Neupert-Laves, et al, *Helv.Chem.Acta.* 60:1861 (1977)), Mn—O (SO$_2$) 2.282 angstroms (Gott, G. et al., *J.Chem.-Soc.Chem.Commun.*, 1283 (1984)), Mn-O (O(Ph)$_3$) 2.084 and 2.147 angstroms (Gott, G. et al, supra). As expected, the Mn-01 distance in Mn(II)-PLED is shorter than the Mn-03 distance due to the greater extent of charge distribution in the carboxylic acid system.

That the manganese atom is in the +2 oxidation state is also supported by comparison of the Mn-N2 to Mn-N distances for divalent manganese (Garrett, T. et al, *Acta.Cryst.* C39:1027 (1983).

EXAMPLE 8

N,N'-bis-(pyridoxal)alkyldiamine-N,N'-diacetic acids

Repeating the procedure of Example 5 but replacing the diamine of Example 3 with the products of Example 4 yields N,N'-bis(pyridoxal)-1,3-(n-propylene)-N,N'-diacetic acid, N,N'-bis(pyridoxal)-1,2-(n-propylene)-N,N'-diacetic acid, N,N'-bis(pyridoxal)-1,2-isopropylene-N,N'-diacetic acid, N,N'-bis(pyridoxal)-1,2-(n-butylene)-N,N'-diacetic acid, N,N'-bis(pyridoxal)-1,4-(n-butylene)-N,N'-diacetic acid, N,N'-bis(pyridoxal)-1,3-(n-butylene)-N,N'-diacetic acid, and N,N'-bis(-pyridoxal)-1,2-(3-methylene)propyl-N,N'-diacetic acid.

EXAMPLE 9

Mn(II) Chelates

Repeating the procedure of Example 7 but replacing N,N'-bis-(pyridoxal)ethylenediamine-N,N'-diacetic acid with equimolar amounts of the products of chelate forming compounds produced in accordance with Example 6, yields the corresponding Mn(II) chelates of N,N'-bis(pyridoxal)-1,3-(n-propylene)-N,N'-diacetic acid, N,N'-bis(pyridoxal)-1,2-(n-propylene)-N,N'-diacetic acid, N,N'-bis(pyridoxal)-1,2-isopropylene-N,N'-diacetic acid, N,N'-bis(pyridoxal)-1,2-(n-butylene)-N,N'-diacetic acid, N,N'-bis(pyridoxal)-1,4-(n-butylene)-N,N'-diacetic acid, N,N'-bis(pyridoxal)-1,3-(n-butylene)-N,N'-diacetic acid, and N,N'-bis(pyridoxal)-1,2-(3-methylene)propyl-N,N'-diacetic acid.

EXAMPLE 10

N,N'-bis(pyridoxal)-trans-1,2-cyclohexylenediimine

A 26.5 gm quantity (0.1 mole) of pyridoxal hydrochloride is dissolved in 200 ml of methanol, and 20 ml of 5 N NaOH is added. Then 5.71 gm (0.05 mole) of trans-1,2-diaminocyclohexane is added with stirring, and the volume of the solution is reduced to 100 ml in vacuo. After cooling to 0° C., the imine is isolated by filtration, washed with diethyl ether, and dried in vacuo to yield N,N'-bis(pyridoxal)-trans-1,2-cyclhexylenediimine or 4-(N-(2-methyl-3-hydroxy-5-hydroxymethyl-4-pyridinylmethylide)-1,2-cyclohexyleneiminomethyl)-2-hydroxy-3-methyl-5-pyridylmethanol.

EXAMPLE 11

N,N'-bis(pyridoxal)-1,2-(cycloalkylene or arylene)diimines

Repeating the procedure of Example 10 but replacing the trans-1,2-diaminocyclohexane with trans-1,2-diaminocyclopetnae, trans-1,2-diaminocycloheptane, trans-1,2-diaminocyclooctane, o-aminoaniline and and cis-1,2-diaminocyclohexane, yields the corresponding N,N'-bis(pyridoxal)-trans-1,2-cyclopentylenediimine, N,N'-bis(pyridoxal)-trans-1,2-cycloheptylenediimine, N,N'-bis(pyridoxal)-trans-1,2-cyclooctylenediimine, N,N'-bis(pyridoxal)-1,2-phenylenediimine, and N,N'-bis(pyridoxal)-cis-1,2-cyclhexylenediimine.

EXAMPLE 12

N,N'-bis(pyridoxal)-trans-1,2-cyclohexylenediamine

A 14 gm (0.02 mole) portion of the diimine product of Example 10 id dissolved in 200 ml of 1:1 water: methanol. The resulting solution is sparged with argon, and 1.0 gm of 5% platinum on carbon is added. The system is flushed with hydrogen. The hydrogen pressure is increased to 50 psig for 16 hr at 25° C. The reaction product is filtered through CELITE, and the resulting solution of N,N'-bis(pyridoxal)-trans-1,2-cyclohexylenediamine or 4-(N-(2-methyl-3-hydroxy-5-hydroxymethyl-4-pyridinylmethyl)-1,2-cyclohexyleneiminomethyl)-2-hydroxy-3-methyl-5-pyridylmethanol is stored at 0° C. until use in Example 14.

EXAMPLE 13

N,N'-bis(pyridoxal)-1,2-(cycloalkylene or arylene) diamines

Repeating the procedure of Example 12 but replacing the diimine product of Example 10 with the diimine products prepared in accordance with the procedure of Example 11 yields the corresponding diamines: N,N'-bis(pyridoxal)-trans-1,2-cyclopentylenediamine, N,N'-bis(pyridoxal)-trans-1,2-cycloheptylenediamine, N,N'-bis(pyridoxal)-trans-1,2-cyclooctylenediamine, N,N'-bis(pyridoxal)-1,2-phenylenediamine, and N,N'-bis(pyridoxal)-cis-1,2-cyclohexyleneenediamine.

EXAMPLE 14

N,N'-bis-(pyridoxal)trans-1,2-cyclohexylenediamine-N,N'-diacetic acid

The diamine from Example 12 is charged to a one liter 3-neck flash, and the pH is adjusted to 11 with 5 N NaOH. Then 5.6 gm (0.04 mole) of bromoacetic acid is dissolved in 10 ml of water and added dropwise to the stirred diamine solution while maintaining the pH at 11. The reaction is warmed to 50° C. and stirred for 16 hr. Then 50 gm of weakly acidic cation exchange resin (AMBERLITE IRC-50) is added. The resin is removed by filtration, and 15 gm of cation exchange resin (DOWEX 50W-X8) is added.

The solution is filtered, and all of the solvent is evaporated from the filtrate. The solid is dissolved in 30 ml of 88% formic acid, and the product is precipitated by the addition of 150 ml of methanol followed by 150 ml of ethanol. The solvent mixture is decanted from the precipitate and discarded. The solid is dissolved in a minimum amount of deionized water (about 100 ml), and the product is allowed to stand overnight at 25° C. The product is isolated by filtration, washed with 50 ml of cold water, 25 ml of ethanol and then dried in vacuo to yield the product. The compound is recrystallized by the same procedure to yield N,N'-bis-(pyridoxal)-trans-1,2-cyclohexylenediamine-N,N'-diacetic acid or N,N'-bis(3-hydroxy-2-methyl-5-hydroxymethyl-4-pyridylmethyl)-trans-1,2-cyclohexylenediamine-N,N'-diacetic acid.

EXAMPLE 15

N,N'-bis-(pyridoxal)-1,2-(cycloalkylene or arylene)diamine-N,N'-diacetic acids

Repeating the procedure of Example 14 but replacing the diamine of Example 12 with the diamines of Example 13 yields the corresponding: N,N'-bis(pyridoxal)-trans-1,2-cyclopentylenediamine-N,N'-diacetic acid, N,N'-bis(pyridoxal)-trans-1,2-cycloheptylenediamine-N,N'-diacetic acid, N,N'-bis(pyridoxal)-trans-1,2-cyclooctylenediamine-N,N'-diacetic acid N,N'-bis(pyridoxal)-1,2-phenylenediamine-N,N-'diacetic acid, and N,N'-bis(pyridoxal)-cis-1,2-cyclohexylenediamine-N,N'-diacetic acid.

EXAMPLE 16

Manganese(II) chelates

Repeating the procedure of Example 7 but replacing N,N'-bis-(pyridoxal)ethylenediamine-N,N'-diacetic acid with equimolar amounts of the products of chelate forming compounds produced in accordance with Examples 14 and 15 yields the corresponding Mn(II) chelates of N,N'-bis-(pyridoxal-)-trans-1,2-cyclohexylenediamine-N,N'-diacetic acid, N,N'-bis(pyridoxal)-trans-1,2-cyclopentylenediamine-N,N'-diacetic acid, N,N'-bis(pyridoxal)-trans-1,2-cycloheptylenediamine-N,N'-diacetic acid, N,N'-bis(pyridoxal)-trans-1,2-cyclooctylenediamine-N,N'-diacetic acid N,N'-bis(pyridoxal)-1,2-phenylenediamine-N,N-'diacetic acid, and N,N'-bis(pyridoxal)-cis-1,2-cyclohexylenediamine-N,N'-diacetic acid.

EXAMPLE 17

PLED-(mono)acetic Acid

Repeating the procedure of Example 5 but using only one molar equivalent of bromoacetic acid yields the corresponding monoacetic acid compound, N,N'-bispyridoxalethylenediamine-N-acetic acid or N,N'-bis(3-hydroxy-2-methyl-5-hydroxymethyl-4-pyridylmethyl-)ethylenediamine-N-acetic acid, In a like manner, repeating the procedures of Examples 8, 14 and 15 with one molar equivalent of bromoacetic acid yields the corresponding monoacetic acid compounds: N,N'-bis(pyridoxal)-1,3-(n-propylene)-N-acetic acid, N,N'-bis(pyridoxal)-1,2-(n-propylene)-N-acetic acid, N,N'-bis(pyridoxal)-1,2-isopropylene-N-acetic acid, N,N'-bis(pyridoxal)-1,2-(n-butylene)-N-acetic acid, N,N'-bis(pyridoxal)-1,3-(n-butylene-N-acetic acid, N,N'-bis(pyridoxal)-1,2-(3-methylene)propyl-N-acetic acid, N,N'-bis-(pyridoxal)-trans-1,2-cyclohexylenediamine-N-acetic acid. N,N'-bis(pyridoxal)-trans-1,2-cyclopentylenediamine-N-acetic acid N,N'-bis(pyridoxal)-trans-1,2-cycloheptylenediamine-N-acetic acid, N,N'-bis(pyridoxal)-trans-1,2-cyclooctylenediamine-N-acetic acid, N,N'-bis(pyridoxal)-1,2-phenylenediamine-N-acetic acid, and N,N'-bis(pyridoxal)-cis-1,2-cyclohexylenediamine-N-acetic acid.

EXAMPLE 18

Manganese(II) chelates

Repeating the procedure of Example 7 but replacing N,N'-bis-(pyridoxal)ethylenediamine-N,N'-diacetic acid with equimolar amounts of the products of chelate forming compounds produced in accordance with Example 17 yields the corresponding Mn(II) chelates of N,N'-bis(pyridoxal)-1,3-(n-propylene)-N-acetic acid, N,N'-bis(pyridoxal)-1,2-(n-propylene)-N-acetic acid, N,N'-bis(pyridoxal)-1,2-isopropylene-N-acetic acid, N,N'-bis(pyridoxal)-1,2-(n-butylene)-N-acetic acid, N,N'-bis(pyridoxal)-1,4-(n-butylene)-N-acetic acid, N,N'-bis(pyridoxal)-1,3-(n-butylene-N-acetic acid, N,N'-bis(pyridoxal)-1,2-(3-methylene)propyl-N-acetic acid, N,N'-bis-(pyridoxal)-trans-1,2-cyclohexylenediamine-N-acetic acid, N,N'-bis(pyridoxal)-trans-1,2-cyclopentylenediamine-N-acetic acid, N,N'-bis(pyridoxal)-trans-1,2-cycloheptylenediamine-N-acetic acid, N,N'-bis(pyridoxal)-trans-1,2-cyclooctylenediamine-N-acetic acid, N,N'-bis(pyridoxal)-1,2- phenylenediamine-N-acetic acid, and N,N'-bis(pyridoxal)-cis-1,2-cyclohexylenediamine-N-acetic acid.

We claim:

1. A chelating compound of the formula:

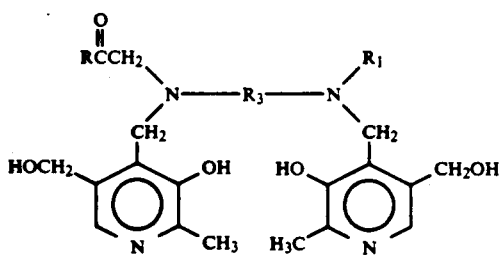 (I)

wherein

R is hydroxy, alkoxy having from 1 to 18 carbons, hydroxy-substituted alkoxy having from 1 to 18 carbons, amino or alkylamido having from 1 to 18 carbons;

$R_1$ is hydrogen or

$R_2$ is hydroxy, alkoxy having from 1 to 18 carbons, amino or alkylamido having from 1 to 18 carbons; and $R_3$ is alkylene having from 1 to 8 carbons, 1,2-cyclalkylene having from 5 to 8 carbons, or 1,2-arylene having from 6 to 10 carbons when $R_1$ is hydrogen, and $R_3$ is 1,2-cycloalkylene having from 5 to 8 carbons, or 1,2-arylene having from 6 to 10 carbons when $R_1$ is other than hydrogen; and the pharmaceutically acceptable water-soluble salts thereof.

2. A chelating compound of claim 1 wherein $R_3$ 1,2-cycloalkylene having from 3 to 8 carbons, or 1,2-arylene having from 6 to 10 carbons.

3. A chelating compound of claim 1 wherein $R_1$ is

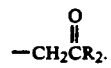

4. A chelating compound of claim 3 wherein R and $R_2$ are preferably each individually hydroxy, alkoxy having from 1 to 8 carbons, ethylene glycol, glycerol, amino or alkylamido having from 1 to 8 carbons.

5. A chelating compound of claim 3 wherein $R_3$ 1,2-cycloalkylene having from 3 to 8 carbons, or 1,2-arylene having from 6 to 10 carbons.

6. A chelating compound of claim 3 wherein R and $R_2$ are hydroxy or a salt thereof.

7. As a chelating compound of claim 1, N,N'-bis-(pyridoxal)-1,2-cycloalkylenediamine-N,N'-diacetic acid or a salt thereof.

8. A chelating compound of claim 1 wherein $R_3$ is 1,2-cyclohexylene.

9. As a chelating compound of claim 8, N,N'-bis-(pyridoxal)-trans-1,2-hexylenediamine-N,N'-diacetic acid or a salt thereof.

* * * * *